United States Patent [19]

Huszar

[11] Patent Number: 4,945,044
[45] Date of Patent: Jul. 31, 1990

[54] OBJECTIVE BIOCHEMICAL METHOD FOR DETERMINING FERTILIZATION POTENTIAL IN OLIGOSPERMIC MEN

[76] Inventor: Gabor B. Huszar, 16 Chestnut Ln., Woodbridge, Conn. 06525

[21] Appl. No.: 255,510
[22] Filed: Oct. 11, 1988
[51] Int. Cl.[5] .............................................. C12Q 1/50
[52] U.S. Cl. ......................................... 435/17; 435/4; 435/29
[58] Field of Search ............................... 435/29, 4, 17

[56] References Cited

PUBLICATIONS

Huszar et al.—Gamete Research, vol. 19 (1988) pp. 67–75.
Huszar et al.—Annals N.Y. Acad. Sci.—Vol. 513 (1987), pp. 602–605.
Wallimann et al.—Chem. Abst. Vol. 104 (1986), page 183729c.
Huszar et al.—Chem. Abst. Vol. 109 (1988), p. 71522b.
Creatine Kinase Activity in Sperm: A possible New Diagnostic Tool of Sperm Function—Gabor Huszar, Lynne Vigue, Society for Gynecologic Investigation (1986).
CPK Activity Reliably Predicts Sperm Quality in Men-n—Gabor Huszar, Lynne Vigue, Society for Gynecologic Investigation (1987).
Serial Sperm CPK Measurements in Oligospermic and Normospermic Men—Gabor Huszar, Lynne Vigue, 5th World Congress of in Vitro Fertilization and Embryo Transfer (1987).
Sperm Creatine Phosphokinase (CPK) Activity is a Predictor of Fertilizing Capacity in Oligospermic Men—Gabor Huszar, Lynne Vigue, American Fertility Society (1987).
Enhancement of Human Sperm Motility and Velocity in Vitro: Effects of Calcium and Creatine Phosphate, Fertility and Sterility—Fakih, MacLusky, DeCherney, Wallman and Huszar, Fertility and Sterility, vol. 46, No. 5, pp. 938–944, (Nov. 1986).
Ratio of B-Type and M-Type Sperm CPK Isoforms Correlates with CPK Activity and Sperm Quality in Oligosphermic Specimens—Huszar, Vigue, Quevedo, Vigue American Fertility Society 1988.
Increased Cellular CPK Concentrations Cause the Elevated Sperm CPK Activities in Oligospermic Specimens—Huszar, Vigue, Society for Gynecologic Investigation (1988).
Directions for Corning Electrophoresis Cardiotrac-CK Creatine Kinase Isoenzyme Substrate Set (Date unknown).
Directions for Helena Laboratories Titan Gel Iso-Dot CK Isoenzyme Procedure (Date unknown).
Beckman Paragon Electrophoresis System Creatine Kinase Isoenzyme Electrophoresis Kit Directions (Date unknown).

Primary Examiner—Sam Rosen
Attorney, Agent, or Firm—DeLio & Associates

[57] ABSTRACT

A method for testing sperm quality comprising obtaining a sperm sample; detecting CK enzyme from the sperm sample; measuring a first CK enzyme concentration for CKX isoforms of the CK enzyme; and determining a sperm quality parameter based upon the first CK enzyme concentration. Preferably a second CK enzyme concentration is measured for CKB isoforms of the CK enzyme and is also used as a basis for determining the sperm quality parameter. Measurements of the levels of CKX and CKB isoforms by electrophoresis and fluorescence techniques are used to establish the first and second CK enzyme concentrations. The sperm quality parameter is proportional to the ratio of the CKX isoform level to the sum of the CKX and CKB isoform levels. Sperm which meets a predetermined minimum sperm quality level is selected for use in vivo or in vitro fertilization attempts on eggs.

13 Claims, 2 Drawing Sheets

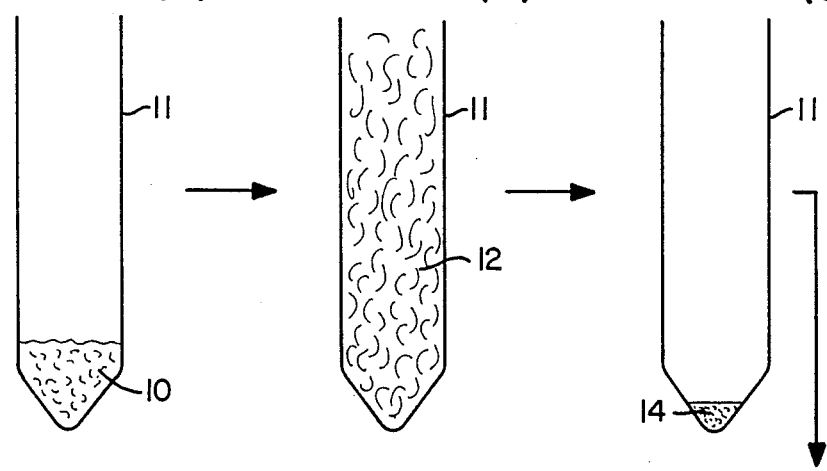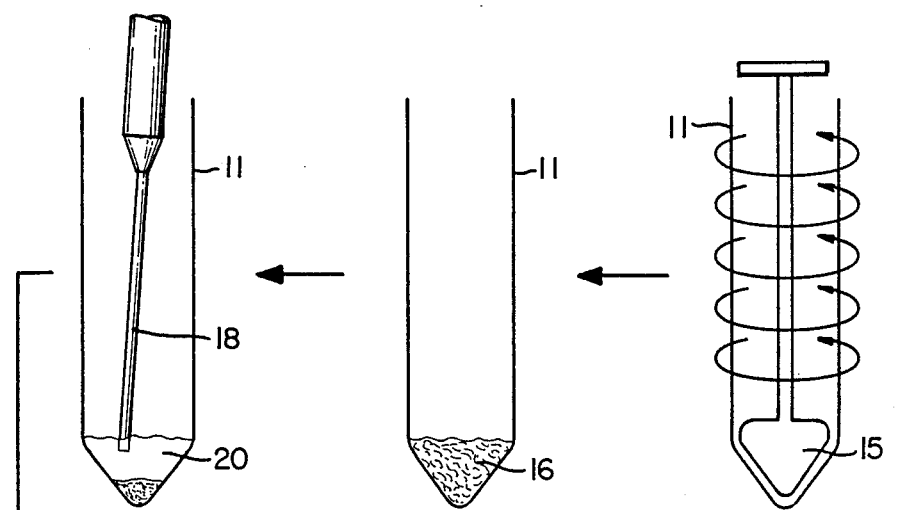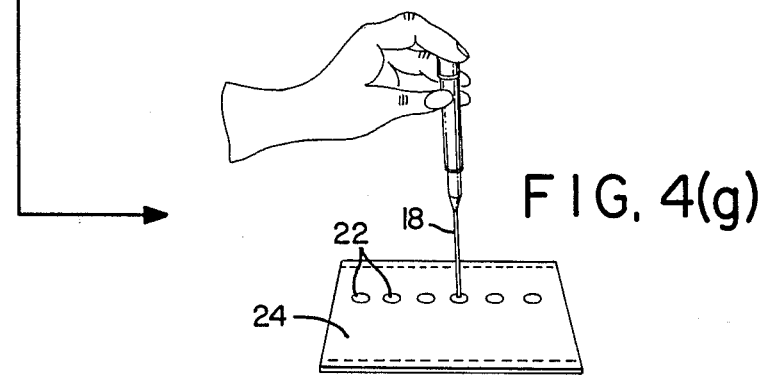

OBJECTIVE BIOCHEMICAL METHOD FOR DETERMINING FERTILIZATION POTENTIAL IN OLIGOSPERMIC MEN

BACKGROUND OF THE INVENTION

This invention relates to a biochemical method for determining the fertilization potential in sperm of oligospermic men and, in particular, to a method which utilizes the separation and measurement of particular enzymes in the cellular physiology of the spermatozoa.

The testicle serves as a site for spermatogenesis, sperm production and sperm maturation. Diagnosis of possible problems in spermatogenesis is normally carried out with the determination of sperm concentrations in the ejaculate. The sperm count fluctuates in all men, but due to the occasional lack of sperm, is more distinct in oligospermic (OS) patients with sperm counts below the $20 \times 10^6$ sperm/ml normal level of normospermic (NS) patients. Low sperm concentrations may be due to pituitary problems, deficient hormone levels, testicular disorders, age, environmental factors, fever or excess heat, exposure to organic solvents in the work place, etc.

It has been found that the incidence of male factor or cause is about 40% in infertile couples. The overwhelming majority of these infertile and subfertile men are oligospermic and/or asthenospermic (sperm motility is lower than 40%). Management problems exist with respect to the oligospermic patients, as these men may try to father children for years because of the absence of methods to predict or establish the fertilizing potential, or lack of it. With intrauterine placement of the sperm or with in vitro fertilization, the pregnancy rates for couples with male factor infertility are only about 20%. This is in spite of the absence of the difference in sperm concentrations and motility among the fertile and infertile oligospermic husbands. It is increasingly apparent that the assessment of sperm quality in oligospermic specimens based on objective biochemical parameters is an essential need for the management of male infertility.

Beyond the classical semen analysis parameters, i.e., sperm concentration, motility and velocity, present approaches to evaluate selected sperm functions include the assessment of motile sperm yield following migration or "swim-up", the cervical mucus penetration test; measurements of acrosine activity, i.e., the enzyme which facilitates sperm penetration; the hypoosmotic sperm swelling procedure which probes the integrity of the sperm membrane; and analysis of sperm motion patterns. None of these tests address the overall physiological soundness of the spermatozoa or show high correlation with fertilizing potential. Even the human sperm zona-free hamster oocyte penetration test, which is a more related biological approach, is more consistent on the negative side (e.g. penetration rates below 15-20% and diminished success in human in vitro fertilization) than it is a measure of fertility.

Bearing in mind the problems in the prior art, it is therefore an object of the present invention to provide an objective biochemical measurement which can predict fertilization potential in oligospermic men.

It is another object of the present invention to provide a method for testing sperm which provides a relatively high degree of accuracy in predicting when fertilization is likely to occur.

It is a further object of the present invention to provide a test of sperm fertilization potential which utilizes a single ejaculate.

It is another object of the present invention to provide a method to determine the cellular maturity of spermatozoa.

SUMMARY OF THE INVENTION

The above and other objects which will be apparent to those skilled in the art are achieved in the present invention which provides a method for testing sperm quality comprising obtaining a sperm sample; detecting CK enzyme from the sperm sample; measuring a first CK enzyme concentration for CKX isoforms of the CK enzyme; and determining a sperm quality parameter based upon the first CK enzyme concentration. Preferably a second CK enzyme concentration is measured for CKB isoforms of the CK enzyme and is also used as a basis for determining the sperm quality parameter. Measurements of the levels of CKX and CKB isoforms by electrophoresis and fluorescence techniques are used to establish the first and second CK enzyme concentrations. The sperm quality parameter is proportional to the ratio of the CKX isoform level to the sum of the CKX and CKB isoform levels. Sperm which meets a predetermined minimum sperm quality level is classified as having a high chance of fertilization and selected for use in in vivo or in vitro fertilization attempts on eggs.

BRIEF DESCRIPTION OF THE DRAWINGS

FIG. 4 is a composite schematic illustration of sperm sample preparation technique for the present invention.

DETAILED DESCRIPTION OF THE INVENTION

The present invention identifies biochemical markers that are important in the cellular physiology of the spermatozoa and provides a method of determining the level of these markers and relating the level to sperm quality and fertilization potential. The marker which has been identified an isoform fraction of the creatine-N-phosphotransferase (CK) enzyme which is the key enzyme in the synthesis and transport of energy as a component of the "creatine phosphate shuttle" demonstrated in the sea urchin sperm. This enzyme and its isoforms have been found to be important because the most essential and energy intense function of sperm is their adenosine triphosphate (ATP) fueled motility (sperm maintain swimming speeds of 40 times their length in each minute, or about 3 miles/hour in human terms).

Figure 1:
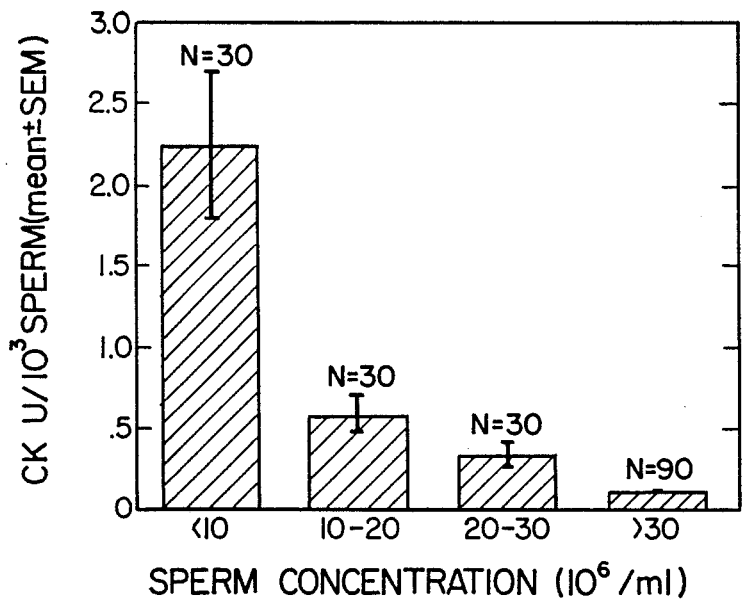
FIG. 1 is a graphical representation of sperm CK enzyme activity for specimens with different sperm concentrations.

In measuring sperm CK activities in oligospermic and normospermic men, it has been found that an inverse correlation exists between the per sperm CK activity and sperm concentrations as shown in the plot in FIG. 1. Measurements of sperm CK activities in the initial semen samples and in sperm fractions enhanced for higher motility and linear velocity by the self-migration selection method indicate that the CK values were lower in the improved fractions. In some oligospermic men the CK-activities of the migrated sperm fractions are similar to that of normospermic men. It is believed that the CK activities in the initial sperm specimen and the degree of improvement in the migrated fractions reflect the relative concentrations of a sperm subpopulation with properties favorable for fertilization, similar to that of fertile normospermic men. CK activity then can be used to predict sperm quality and fertilizing potential of oligospermic men and provides a new technique in semen analysis and in the management of male infertility patients.

The CK enzyme may be made up of more than one isoform otherwise identical in enzymatic activity but having differences in amino acid sequence arising from different genes. Three isoforms of CK have been previously identified in human tissues: muscle-type (M), brain-type (B) and mitochondrial-type ($M_i$). The CK isoforms occur as MM, M, BB or $M_iM_i$ dimers. Many organs contain CK, but the distribution of isoforms is characteristically different. Brain, stomach, intestine, bladder and lung contain primarily the BB isoform dimer of the CK enzyme. While developed skeletal muscle is very rich in the MM dimer, fetal skeletal muscles have been shown to contain primarily the B-type CK enzyme. The gene which directs the synthesis of the M-type CK enzyme has been found to be activated later during the muscle developmental process.

The present invention is based in part on the discovery that, similarly to the differences found in immature and developed muscle, in sperm there may also be found differences in constituent CK isoform concentrations that are specific for the immature sperm cells and mature fertile sperm cells. It has been unexpectedly discovered that sperm which is from oligospermic specimens and has high CK activity contains high levels of the B-type sperm CK enzyme isoform (also referred to as "CKB"). However, men who are normospermic and fertile have, in addition to CKB, a different sperm CK enzyme isoform which will be identified herein as the X-type enzyme isoform (also referred to as "CKX"). This CKX isozyme is similar to the M-type isoform of CK enzyme, but has been found to have about an 8% difference in retardation factor compared to the muscle type M isoform on agarose electrophoresis and occupies a distinctly different position. Also, the sperm CKX isozyme, in contrast with muscle type M, does not form the MB hybrid in vivo or in vitro under the experimental conditions in which muscle CPM combines with the sperm CPB heterodimers. The CKX and CKM isomers also differ in response to various enzyme inhibitors.

Figure 2:
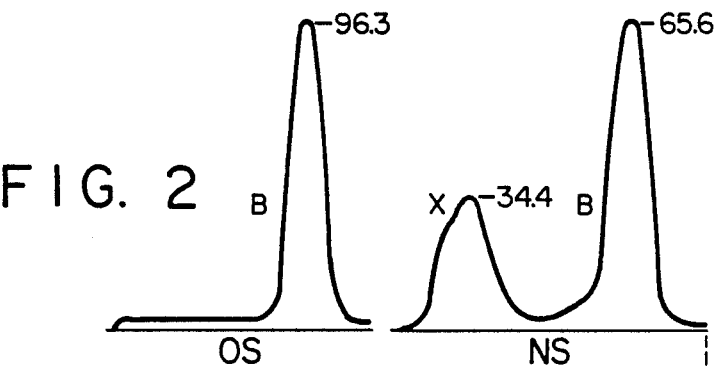
FIG. 2 illustrates different fluorescent measurements of CKX and CKB isoforms in typical oligospermic and normospermic patients' sperm samples.
Figure 3:
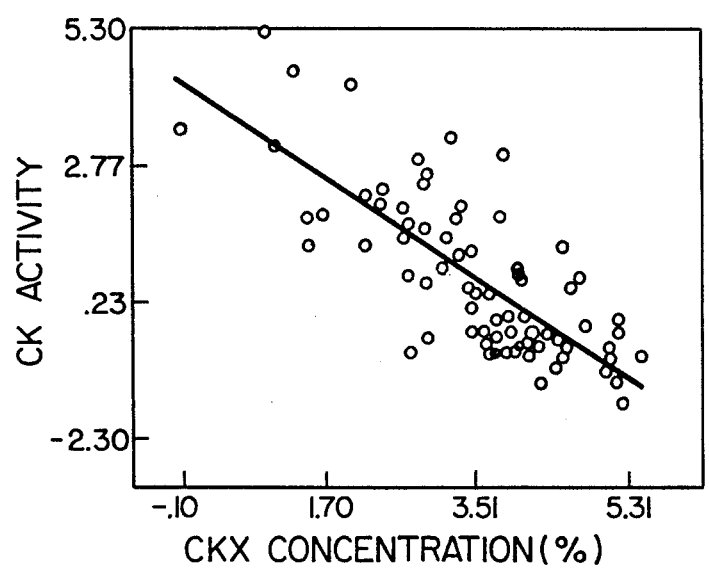
FIG. 3 is a plot of the correlation between sperm CK activity and CKX isoform concentrations in 94 semen specimens.

To testing of the method and system of the present invention, examination was made of correlation between sperm CK activity and the concentrations of the sperm CKX in various oligospermic and normosepermic specimens. In the oligospermic patients, the CKX concentration was very low, and some of the severely oligospermic patients had only the CKB isoform and no detectable CKX. FIG. 2 illustrates a typical comparison of the scanning fluoremetric patterns on electrophoretically separated CKX and CKB isoforms of sperm. In the left-hand graph, a severely oligospermic patient's sperm sample had only CKB isomer. In a normospermic patient's sample on the right, CKX isoform is present in addition to the CKB isoform. As shown in FIG. 3, a plot of the sperm CK activity as a function of CKX concentrations for 94 observations showed the two to be proportional and to have a high correlation factor ($r=0.87$) and high significance ($p<0.001$). The correlation between sperm CKX concentrations and fertilizing potentials have also been examined and found to predict the fertilizing potential of men.

In addition to its method aspect, the present invention provides a system for the determination of sperm quality and fertilizing potential which may be packaged in kit form. The test system and kit is intended to be used by andrology laboratories, and by specialty offices of urologists and fertility specialists. Due to the multiple sample handling capabilities of some existing CK electrophoretic equipment, the test may also be used in mass screening of men for toxic environmental hazards at the work place, in the armed forces, etc.

The method for the detection of sperm CPK isoform ratios is composed the phases of: (1) preparation of the sperm sample from semen; (2) Quantitatively making the CK isoform accessible to detection and measurement by electrophoresis of the sperm CK isoforms; (3) Development of CK activity with the NADH fluorescent technique. (4) Photometric detection of the CK activity and the integration and measurement of the CKX and CKB isoform ratios. These are used to determine the CKX/(CKB+CKX) ratio which is the measure of sperm quality.

As shown in FIG. 4, the sample preparation includes (a) obtaining and preparing a sperm sample 10 in a test tube or vial 11, (b) adding to the sample by centrifugation a sperm washing solution 12 while agitating, and (c) concentrating the washed sample by centrifugation to obtain a sperm pellet 14. A homogenizing solution is then added to the pellet and (d) homogenized with a stirrer or plunger 15 to produce (e) a sperm homogenate 16. The sperm homogenate is then (f) centrifuged to clarify it. A pipette 18 is used to take an aliquot of the sperm supernatant extract 20 which is then (g) deposited in separate wells 22 in electrophoresis plate 24.

Proper specimen collections and washing of the sperm for removal of seminal fluid is important to obtain an accurate interpretation of CK isoenzyme analysis. If the determination is not carried out immediately after collection, the washed sperm pellet covered with a buffer containing an —SH group protectant should be refrigerated and it may be stored for up to 48 hours at 4° C. Alternatively, the sperm pellets may be stored frozen at —20° C. for up to several weeks without loss of activity. Repeated freezing and thawing destroys CK activity and should be avoided.

The determination of sperm CK isoform may be accomplished by using the type of equipment and compositions used by clinical laboratories for the determination of CK ratios in serum of patients for the assessment of myocardial damage. These include the reagents for electrophoresis, the agarose or cellulose acetate gels for the electrophoretic separation of CK enzymes, and the reagents for the detection of activity. The fluorescent detection and scanning, as well as the integration of the activity peaks, is usually carried out by an automatic instrument, which is adapted to the plates of the respective manufacturer, to measure CK isoform levels.

Among the various methods for the separation of the CK isoenzymes, electrophoretic techniques are the most effective and relatively accurate. The isoenzymes of CK are separated by electrophoresis in an agarose medium. The distinctly separated zones containing the isoenzymes are detected by overlaying the agarose with creatine kinase substrate. The presence and activity of the CK-isoforms are detected by their enzymatic activity. CK catalyzes the transfer of phosphate from creatine phosphate to an adenosine diphosphate (ADP) forming creatine and adenosine triphosphate (ATP). The ATP formed in the CK reaction is used to produce glucose-6-phosphate. This reaction is catalyzed by the enzyme hexokinase. As glucose-6-phosphate is formed, ADP is regenerated keeping its concentration at a constant level. The glucose-6-phosphate is then oxidized by the enzyme, glucose-6-phosphate deyhdrogenase with a simultaneous reduction of nicotinamide adenine dinucleotide (AND) to NADH, the fluorescent derivative. The CK substrate contains all the reagents necessary for these reactions and after incubation, the NADH fluorescence which is proportional to the activity of the CK-isoforms is quantified on the electrophoretic film by a scanning fluoremeter.

EXAMPLE

The preferred procedure for testing sperm according to the method of the present invention is as follows:

The sperm test method of the present invention utilizes a kit composed of four concentrated reagents which may be reconstituted prior to use with the addition of distilled water, a 15 ml graduated conical test tube with matching plunger which is used for homogenization, and transparent agarose or cellulose acetate electrophoretic plates for electrophoresis of the CK isoforms.

Reagents (1) Sperm washing solution, (Phosphate buffer-normal [0.15M]saline, pH:7.01).
(2) Sperm homogenization solution, (Phosphate buffer-normal saline, pH:7.0, 20 mM DTT, 0.1% Triton).
(3) The electrophoretic buffer solution: MES (2-(N-Morpholino) ethane sulfonic acid) pH 6.2.
(4) CK substrate, (one ml of this solution is used to dissolve 1 vial of CK substrate).

| Active Ingredients | Final Concentration In Reagent |
|---|---|
| Creatine Phosphate | 90 mM |
| Adenosine Diphosphate | 12 mM |
| Magnesium$^{+2}$ | 60 mM |
| Adenosine Monophosphate | 15 mM |
| Nicotinamide Adenine Dinucleotide | 6 mM |
| Glucose | 60 mM |
| NAC | 60 mM |
| Hexokinase | $9 \times 10^3$ IU/L (30° C.) |
| Glucose-6-phosphate Dehydrogenase | $7.5 \times 10^3$ IU/L (30° C.) |

Sample Preparation (1) The sperm should be separated from the seminal fluid and washed in the sperm washing solution as soon as possible after collection; (2) The sperm pellet after centrifugation should be homogenized (10 turns with the stirrer or plunger) in 0.2 ml of homogenization solution; (3) The sperm homogenate is clarified by centrifugation, and (4) 0.001 ml, 0.002 ml, and 0.005 ml aliquots of the sperm extract are subjected to electrophoresis.

If the test cannot be run within 3 hours of collection, the sperm pellet should be overlaid by about 0.2 ml homogenization solution and it may be stored refrigerated for three days or frozen ($-20°$ C.) up to two months. Repeated freezing and thawing will inactivate the enzyme.

Electrophoresis Procedure (1) Place the reconstituted MES buffer in each chamber of the electrophoresis cell. Level the buffer in both chambers, wipe moisture off center partition; (2) Gently peel the agarose or cellulose acetate electrophoresis plate from its hard plastic cover, being careful to handle the film only by its edges; (3) Apply three different aliquots of the sample to three sample wells (typically 0.001, 0.002, 0.005 ml) to provide allowance for activity differences in the various samples. Samples should be applied using a quantitative microliter dispenser and disposable sample tip. Use a fresh tip for each sample. Touch the drop to the well; do not touch the pipette tip to the well or the plate surface. Apply samples as quickly as possible. After sample application, allow the sample to diffuse into the agarose for one minute; (4) Insert the loaded agarose film into the electrophoresis cell agarose side down, matching the anode ($+$) side of the agarose film with the anode ($+$) side of the cell and (5) Turn on power supply, adjust it to provide adequate current. Typically, 90 volts is used and 20 minutes is allowed for the electrophoresis.

Visualization of the CK-isoform Bands (1) Following electrophoresis, drain the excess buffer from the cell, grasp the agarose film by its edges and remove it. Place the film, agarose side up on a flat counter top with the cathode ($-$) edge toward you; (2) Blot residual buffer from the end of the agarose with a single folded wipe along the gel; (3) Place a 5 ml serological pipette lengthwise along the cathode ($-$) edge of the agarose film; (4) Evenly dispense 1 ml of substrate onto the agarose surface along the edge of the 5 ml serological pipette which faces the anode; (5) To spread the substrate, slowly push the pipette across the agarose film to the beginning of the blotted region at the anode ($+$) edge; (6) Insert the agarose film, agarose side up, in the prewarmed incubator tray on moistened blotting paper and incubate the plate at 37° C. for 20 minutes; (7) Following incubation, place the agarose film in a drying incubator/oven. Dry for 15–20 minutes or until dry; (8) Inspect the dried agarose film under ultraviolet light (at 365 nm). The site of CK isoenzyme activity appears as blue-white fluorescent bands; (9) Scan the agarose film using a photometric scanner having excitation wavelength of 365 nm and which detects the emission wavelength of 460 nm.

In a blind test of 47 semen samples which were subject to in vitro fertilization attempts, good correlation was found between the sperm quality parameter (CKX/CKX+CKB) and resulting pregnancies. Based on the CKX/CKX+CKB ratio, we have classified the samples into very low chance of fertilization (10 samples), intermediate chance of fertilization (8 samples), and high chance of fertilization (29 samples) groups. The 47 semen samples resulted in 56 embryos and 9 pregnancies. In the 10 sperm samples which were classified as having low chance for successful fertilization, there were only 5 of the embryos and none of the pregnancies. In the 8 samples which were rated as being intermediate in fertilization potential there were 9 of the embryos and 2 of the pregnancies. The 27 samples which were rated as having a good chance for fertilization were found to have 42 of the embryos and 7 of the pregnancies. The level of the sperm quality parameter ratio needed for fertilization is estimated to be at least about 0.10. There are slight variations (plus or minus 5%) in detection levels depending on the electrophoretic film and the fluorescent detection system by various manufacturers. However, the values are consistent using the same system.

Thus the present invention provides a useful and long sought method to provide quantative assessment of sperm maturity and fertilizing potential based on a sperm parameter alone, such as the activity ratio of the CKX-type isoform to the total of the CKX-type and CKB-type isoforms within a single ejaculate. The concentration of sperm CKX enzyme is proportional to the presence of a mature sperm sub-population in the specimen. Following determination of the sperm quality parameter, sperm having a predetermined minimum level (e.g., a ratio of at least 0.10) can be selected for attempts to fertilize human eggs by in vivo or in vitro techniques, optionally, including sperm selection by sperm enhancement techniques prior to fertilization attempts.

Additionally, the quantitative assessment of sperm quality by these biochemical parameters serve also as a measure of improvement in optional sperm enhancement procedures, such as swim-up selection, sperm self migration, or various column separation and gradient centrifugation techniques. The CKX concentrations reflect the presence of various sperm sub-populations in ejaculates and in sperm fractions prepared by the various sperm enhancement methods.

The biochemical techniques utilizing CK isoform ratios in accordance with the present invention provide a measure of cellular maturity of spermatozoa and, in the future, may allow the selection of single fertile spermatozoa for the use of advanced reproductive techniques, i.e., sperm injection into oocytes.

The present invention also provides a diagnostic tool which will lead to in vitro repair of sperm defects. A biochemical marker such as CKX permits the assessment of changes in sperm quality, and may be used as an effective screening procedure in an industrial setting where male workers are exposed to toxic conditions. In addition, the CKX ratio will permit the monitoring of spermatogenesis in male patients who are treated with various drugs and during aging. Also, one may monitor the efficacy of male contraceptive techniques in which hormone or peptide analogues temporarily reduce or alter spermatogenesis. After the termination of such treatments, CKX concentrations will indicate the resumption of normal spermatogenesis and will monitor whether the sperm quality in a particular man has reached that of the pre-treatment levels.

Determination of CKX concentrations in accordance with the present invention can also be used to describe the quality of sperm in animals, such as stallions and bulls, and in order to predict fertilizing potential and breeding proficiency.

While this invention has been described with reference to specific embodiments, it will be recognized by those skilled in the art that variations are possible without departing from the spirit and scope of the invention, and that it is intended to cover all changes and modifications of the invention disclosed herein for the purposes of illustration which does not constitute departure from the spirit and scope of the invention.

Having thus described the invention, what is claimed is:

1. A method for testing sperm quality comprising the steps of:
   (a) obtaining a sperm sample;
   (b) detecting sperm CK enzyme from said sperm sample;
   (c) measuring a CK enzyme concentration for CKX isoforms of said CK enzyme; and
   (d) determining a sperm quality parameter based upon the CK enzyme concentration wherein an increased concentration of said CKX isoform indicates a higher chance of fertilization by said sperm sample.

2. The method of claim 1 including a step of measuring a second CK enzyme concentration for CKB isoforms of said CK enzyme, and wherein said step (d) determination of sperm quality parameter is also based upon the second CK enzyme concentration.

3. The method of claim 2 wherein said CK enzyme concentrations are measured by the activity parameters of CKX and CKB isoforms, and wherein said sperm quality parameter is proportional to the ratio of the CKX isoform concentration to the sum of the CKX and CKB isoform concentration with a higher ratio indicating a higher chance of fertilization by said sperm sample.

4. The method of claim 3 wherein said sperm sample is subjected to electrophoresis to detect and measure said CK enzyme isoforms.

5. The method of claim 4 wherein, following electrophoresis, said CK enzyme is reacted to form a derivative product, and said derivative product is fluorescent in proportion with the enzymatic activity of the said CKX and CKB isoforms.

6. The method of claim 1 further including a step between steps (a) and (b) of quantitatively making the CK isoform accessible to detection and measurement.

7. The method of claim 1 further including the step of:
   (e) selecting sperm which meets a predetermined minimum level of said sperm quality parameter for use in in vivo or in vitro fertilization attempts.

8. The method of claim 3 further including the step of:
   (e) selecting sperm which meets a predetermined minimum level of said sperm quality parameter for use in in vivo or in vitro fertilization attempts.

9. The method of claim 8 wherein said minimum sperm quality parameter level is about 0.10 as determined by the ratio of CKX isoform concentration to the total of CKX and CKB isoform concentrations.

10. The method of claim 7 wherein the sperm quality parameter of the selected sperm is examined following sperm enhancement techniques prior to fertilization attempts.

11. A multipart system for determining the quality and the fertilization potential of a sperm sample by measuring sperm CK enzyme concentration for CKX isoforms wherein an increased concentration of CKX isoform indicates a higher chance of fertilization by said sperm sample comprising:
   a sperm washing solution;
   a sperm homogenization solution;
   an electrophoretic buffer solution;
   an electrophoresis film for detecting CK enzyme in sperm samples; and
   a CK substrate composition for forming a fluorescent derivative proportional to the activity of electrophoretically separated CKX and CKB isoforms.

12. The system of claim 10 in kit form wherein said solutions and said CK substrate composition are in concentrated form for aqueous dilution prior to use.

13. The system of claim 12 further including a container and homogenization means for use with said sperm washing and homogenization solutions.

* * * * *

UNITED STATES PATENT AND TRADEMARK OFFICE
CERTIFICATE OF CORRECTION

PATENT NO. : 4,945,044
DATED : Jul. 31, 1990
INVENTOR(S) : Gabor B. Huszar

It is certified that error appears in the above-identified patent and that said Letters Patent is hereby corrected as shown below:

In the Abstract:

Second to the last line, insert "in" after preexisting "in" and before "vivo".

In the Specification:

Column 3, line 19, delete "M" and substitute therefor --MB--.

Column 5, line 11, delete "(AND)" and substitute therefor --(NAD)--.

Signed and Sealed this

Twenty-ninth Day of October, 1991

Attest:

HARRY F. MANBECK, JR.

Attesting Officer

Commissioner of Patents and Trademarks